United States Patent
Makino et al.

(10) Patent No.: US 10,048,227 B2
(45) Date of Patent: *Aug. 14, 2018

(54) SURFACE PROPERTY INSPECTION METHOD AND APPARATUS

(71) Applicant: SINTOKOGIO, LTD., Nagoya-shi, Aichi (JP)

(72) Inventors: Yoshiyasu Makino, Toyokawa (JP); Hideaki Kaga, Toyokawa (JP)

(73) Assignee: SINTOKOGIO, LTD., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/128,573

(22) PCT Filed: Oct. 8, 2014

(86) PCT No.: PCT/JP2014/076901
§ 371 (c)(1),
(2) Date: Sep. 23, 2016

(87) PCT Pub. No.: WO2015/145833
PCT Pub. Date: Oct. 1, 2015

(65) Prior Publication Data
US 2017/0108470 A1 Apr. 20, 2017

(30) Foreign Application Priority Data
Mar. 24, 2014 (JP) ................ 2014-060368

(51) Int. Cl.
*G01N 27/90* (2006.01)
*B24C 1/10* (2006.01)

(52) U.S. Cl.
CPC ..... *G01N 27/9046* (2013.01); *G01N 27/9033* (2013.01); *B24C 1/10* (2013.01)

(58) Field of Classification Search
USPC ................ 324/209, 225, 227, 234
See application file for complete search history.

(56) References Cited

U.S. PATENT DOCUMENTS 3,135,914 A * 6/1964 Callan ............... G01N 27/9046
324/227
5,744,954 A * 4/1998 Soules .................. G01N 27/72
324/225
(Continued)

FOREIGN PATENT DOCUMENTS

EP  2 707 705 A1  3/2014
EP  3 098 600 A1  11/2016
(Continued)

OTHER PUBLICATIONS

International Search Report and English language translation thereof, in corresponding International Application No. PCT/JP2014/076901, dated Dec. 22, 2014, 5 pages.
(Continued)

*Primary Examiner* — Vincent Q Nguyen
(74) *Attorney, Agent, or Firm* — Brinks Gilson & Lione

(57) ABSTRACT

The present invention provides a surface property inspection method and apparatus for inspecting the surface properties of a test object subjected to two stages of shot peening. The present invention is an apparatus 1 includes an AC power supply, an AC bridge circuit, and an evaluation apparatus. The AC bridge circuit is constituted by a variable resistor, a reference detector and inspection detector. The inspection detector includes a coil wound so as to oppose the surface property inspection area of the test object M; an eddy current is excited in the test object M by supplying AC power to the coil. A pass/fail judgment of the first shot peening can be made by inspecting the surface properties of a test object subjected to a second shot peening only after the second shot peening is completed.

11 Claims, 9 Drawing Sheets

(56) References Cited

U.S. PATENT DOCUMENTS

| | | | |
|---|---|---|---|
| 5,898,302 A | 4/1999 | Soules | |
| 7,112,960 B2 * | 9/2006 | Miller | B24B 37/013 |
| | | | 324/228 |
| 2008/0001609 A1 | 1/2008 | Kojima et al. | |
| 2012/0126803 A1 * | 5/2012 | Goldfine | G01R 33/0064 |
| | | | 324/239 |
| 2013/0035878 A1 * | 2/2013 | Wesby | F03D 7/042 |
| | | | 702/42 |
| 2014/0084910 A1 | 3/2014 | Makino | |
| 2016/0341699 A1 | 11/2016 | Makino et al. | |

FOREIGN PATENT DOCUMENTS

| | | |
|---|---|---|
| JP | 55-007630 A | 1/1980 |
| JP | 05-203503 A | 8/1993 |
| JP | 10-217122 A | 8/1998 |
| JP | 2008-002973 A | 1/2008 |
| JP | 2013-529286 A | 7/2013 |
| TW | 201300772 | 1/2013 |

OTHER PUBLICATIONS

Extended European Search Report in corresponding European Application No. 14887432.4, dated Oct. 30, 2017, 8 pages.

\* cited by examiner

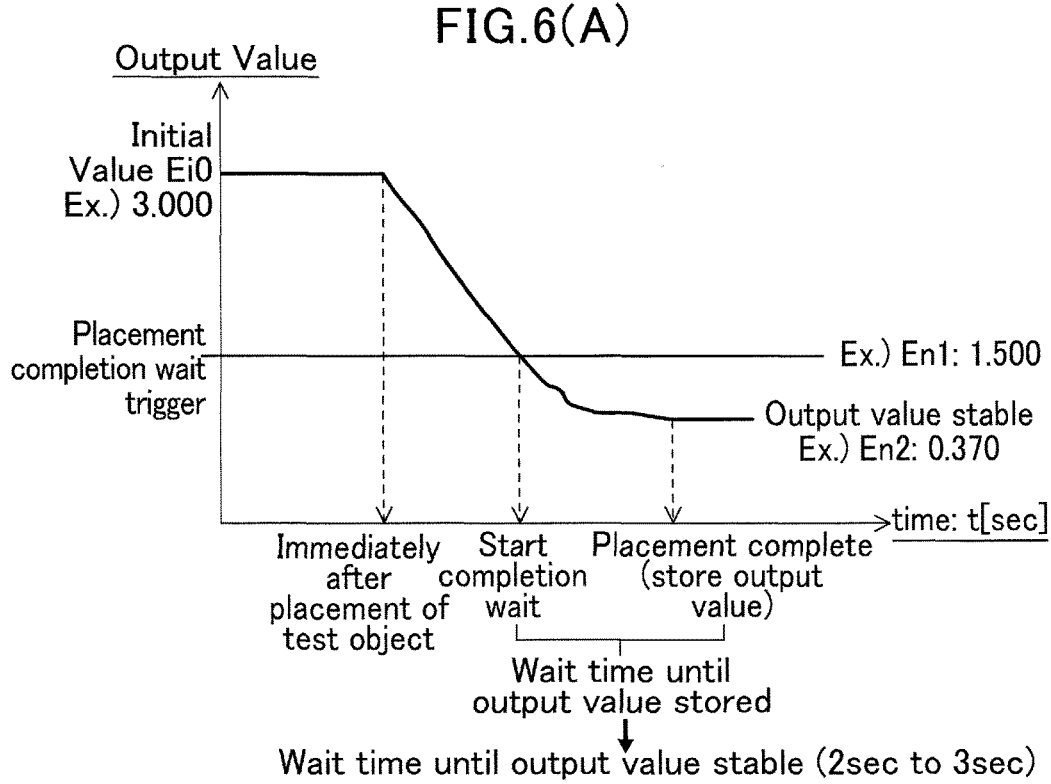
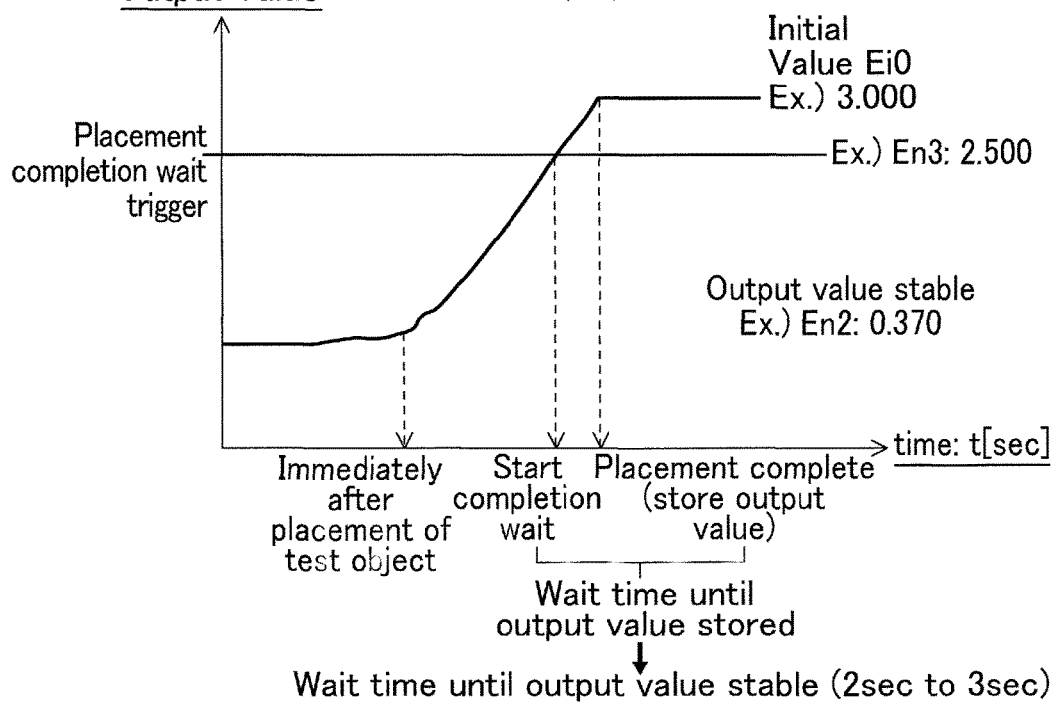

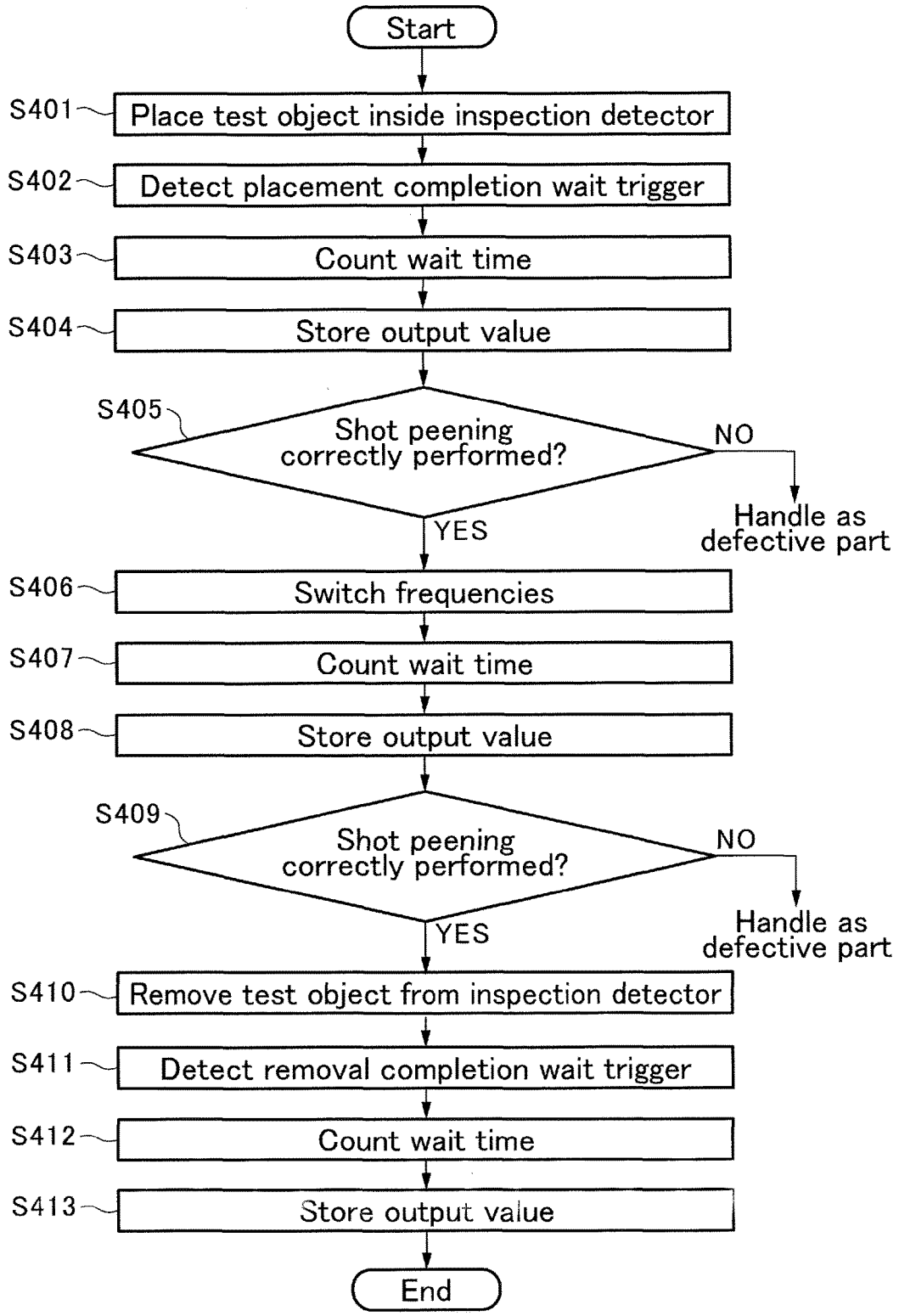

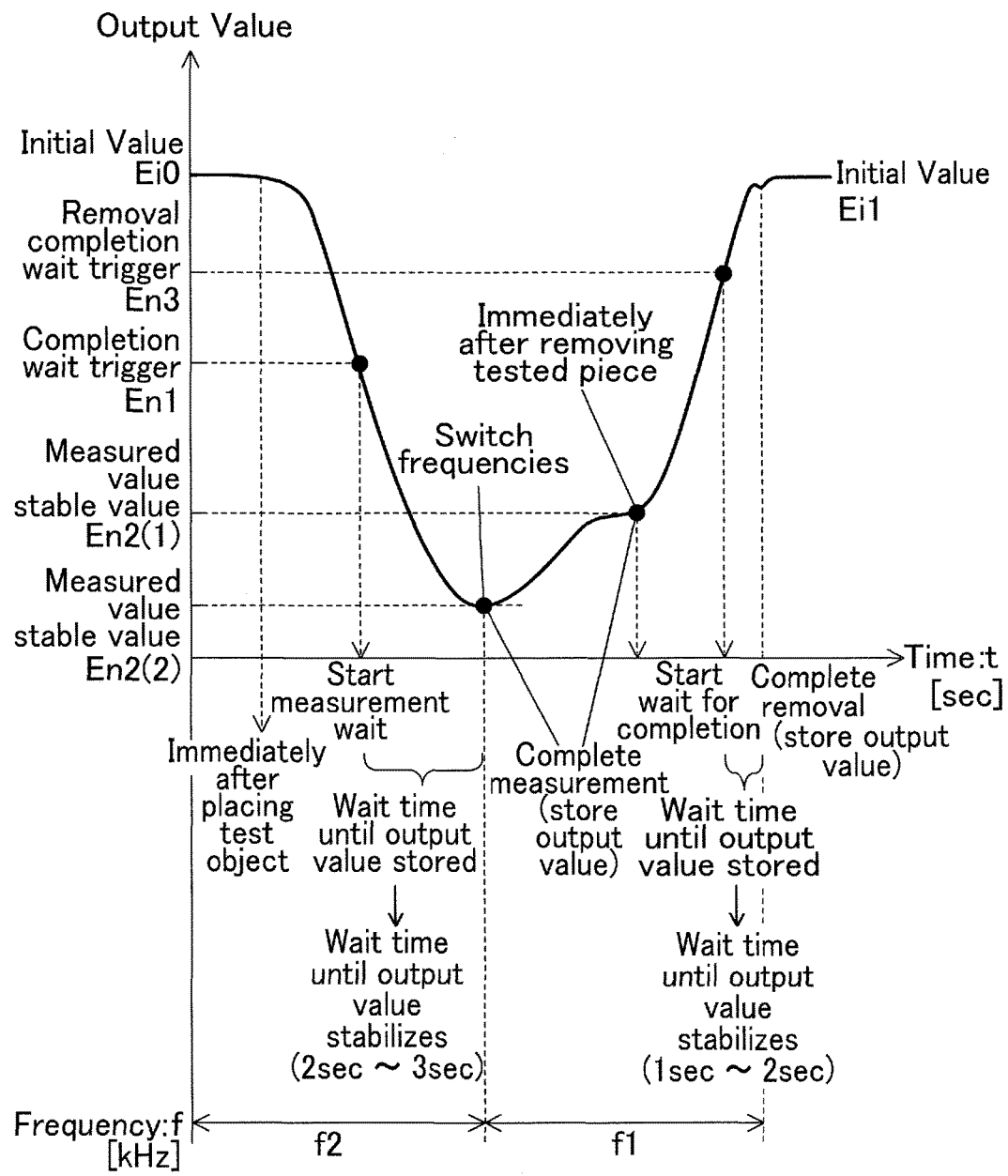

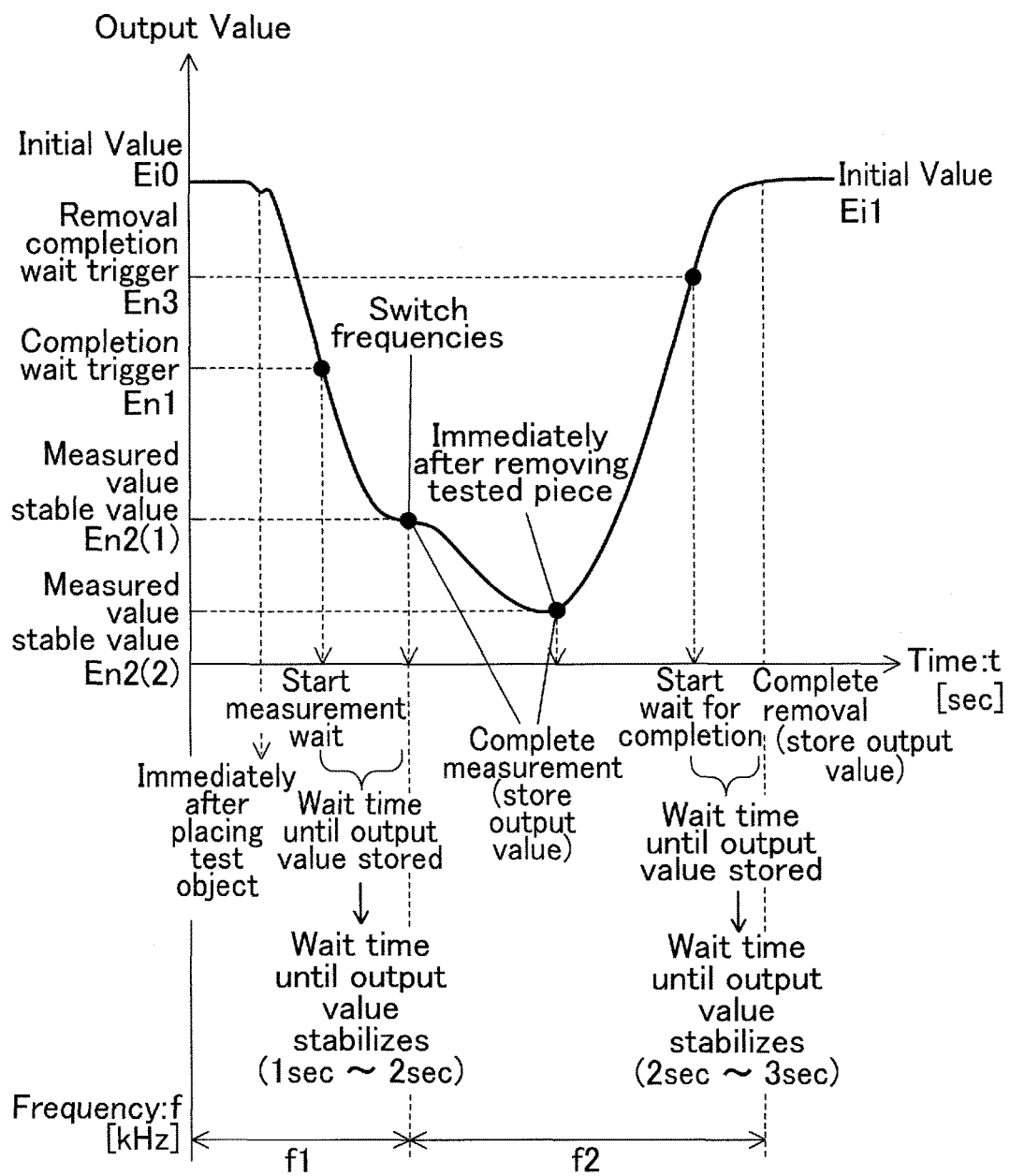

SURFACE PROPERTY INSPECTION METHOD AND APPARATUS

This application is a 371 application of PCT/JP2014/076901 having an international filing date of Oct. 8, 2014, which claims priority to JP2014-060368 filed Mar. 24, 2014, the entire contents of which are incorporated herein by reference.

TECHNICAL FIELD

The present invention pertains to a surface property inspection method and surface property inspection apparatus for inspecting the surface properties of a test object such as a steel part or the like which has been subjected to shot peening in two stages under different conditions, with the object of improving fatigue strength or the like.

BACKGROUND ART

For some time, shot peening has been applied in order to improve fatigue strength by imparting compressive residual stress to steel products such as automobile parts, dies, and the like.

In this type of shot peening, a two stage peening is performed, whereby shot peening is carried out under relatively high strength peening conditions using a large projection material, then shot peening is performed under lower strength peening conditions to optimize the distribution of residual stress.

For example, Patent Document 1 discloses a technology for changing the hardness and particle size of a heat treated mold (steel product) by appropriately changing the hardness and particle size of spherical projection material (shot) and performing multiple peening iterations.

PRIOR ART REFERENCES

Patent References

Patent Document 1: Japanese Published Unexamined Patent Publication H.10-217122

SUMMARY OF THE INVENTION

Problems to be Solved by the Invention

As a method for determining whether such two stage peening has been correctly performed, inspection by a sensing pin surface roughness tester, roughness inspection by a laser microscope, and X-ray stress measurement methods have been employed following the second peening stage, but each requires measurement time, and full inspection of all parts is difficult. It is also not possible to evaluate the entirety of a surface subjected to surface treatment. There is also the problem of being unable to determine whether the first stage peening, which is the first performed, has been appropriately carried out. Conceivable cases in which the first stage peening has not been appropriately performed include cases in which the first stage peening was not implemented, and cases in which the desired residual stress was not imparted.

It is difficult to determine the presence or absence of first stage peening by visual inspection, and conducting visual inspections after the first stage peening and second stage peening, respectively, results in an increase in inspection person hours.

The present invention therefore has the object of providing, in a surface property inspection method and surface property inspection apparatus for inspecting the surface properties of a test object subjected to two stages of shot peening, a surface property inspection method and surface property inspection apparatus capable of judging, in a single inspection performed after completion of second stage peening, whether residual stress has been appropriately applied in the first stage of shot peening.

Means for Resolving Problems

To achieve the above object, the following technical means are used in the invention of claim 1: a surface property inspection method for inspecting a surface property of a shot peened test object, comprising steps of: an inspection apparatus preparation step for preparing a surface property inspection apparatus, wherein the surface property inspection apparatus comprises: an AC bridge circuit; an AC power supply for supplying AC power to the AC bridge circuit; and an evaluation device for evaluating the surface property of the test object based on an output signal from the AC bridge circuit; wherein the AC bridge circuit comprises: a variable resistor in which the distribution ratio can be varied between a first resistor and a second resistor, an inspection detector comprising a coil capable of exciting AC magnetism, formed so that said coil can be disposed to excite an eddy current in the test object, and a reference detector, in which a reference test object having the same structure as the test object is disposed, and detecting a reference state which serves as a reference for comparison with an output from the inspection detector; and wherein the first resistor, the second resistor, the reference detector, and the inspection detector constitute the bridge circuit; a threshold value setting step for determining a threshold value used in evaluating the surface property of the test object in the evaluation device; an eddy current excitation step for exciting the eddy current by the inspection detector in the test object subjected to a first shot peening for imparting residual stress from a surface into deep portions and a second shot peening for performing, after the first shot peening, a lower strength shot peening than the first shot peening, thereby imparting further residual stress close to the surface; and a pass/fail judgment step for using the evaluation device to compare the threshold value with the output signal output from the AC bridge circuit during the eddy current excitation step implemented after the second shot peening, and then judging whether the first shot peening was correctly performed.

Using the invention of claim 1, an eddy current can be excited in a test object by an inspection detector coil, and the surface properties of the test object can be evaluated by comparing the output signal output from an AC bridge circuit to a threshold value. This enables high precision inspection of the surface state using a simple circuit configuration. Also, a method is adopted in which an eddy current is excited in the test object to inspect surface properties, therefore the effects of temperature variations on the inspection environment can be reduced.

Because a reference test object of the same structure as the test object is used to detect a reference state in a reference detector, fluctuations in output values due to changes in the inspection environment such as temperature, humidity, and magnetism will be the same as in the test object. Fluctuations in output values caused by changes in the inspection environment such as temperature, humidity, or magnetism can thus be canceled, and measurement accuracy improved.

By inspecting the surface properties of a test object subjected to a two stage shot peening comprising a first shot peening and a second shot peening only after the second shot peening, an inspection can be made of whether residual stress has been correctly imparted over a range, for example, of approximately 30-100 μm from the surface, to judge the quality of the first shot peening. By so doing, a judgment of whether the second stage peening has been correctly performed can be made by a single inspection after performing the two stage shot peening, thereby shortening inspection time. Inspection can also be quickly and non-destructively performed, making this method suitable for inline inspection, as well.

Here the term "same structure" means the same materials and shape, whether or not surface treatment is applied. Also, "surface properties" means "properties from the most outermost surface of the test object to the interior layer of influence." "Whether the first shot peening has been correctly performed" is a concept which includes the pass/fail of the first shot peening as well as whether the first shot peening has been implemented.

The invention of claim 2 uses a technical means whereby the eddy current excitation step is performed under the state that the reference test object which is an untreated object, not subjected to surface treatment, is placed in the reference detector.

As in the claim 2 invention, when an untreated part not subjected to surface treatment is used as a reference test object, the output based on the difference between the surface state of that part and the test object can be increased, measurement accuracy can be further improved, and the threshold value more easily set, making this preferable.

In the invention of claim 3, a technical means is used whereby in the surface property inspection method of claim 1 or 2, in the threshold value setting step, the threshold value is determined based on the output signal from the AC bridge circuit when the eddy current is excited in the test object on which the first shot peening and second shot peening have been correctly performed.

Using the claim 3 invention, setting of a threshold value is performed based on the output characteristics of a test object on which a first shot peening and second shot peening have been correctly performed, therefore an accurate judgment can be made as to whether the first shot peening and second shot peening have both been correctly performed.

In the invention of claim 4, a technical means is used for the surface property inspection method of any one of claims 1 to 3, further comprising steps of: a second eddy current excitation step wherein which AC power at a higher frequency than that of the eddy current excitation step is supplied by the AC power supply to excite the eddy current in the test object, and a second pass/fail judging step wherein the evaluation device judges whether the second shot peening has been appropriately performed, based on the output signal from the AC bridge circuit when the eddy current is excited during the second eddy current excitation step.

In the surface property inspection method of the present invention, information reflecting residual stress close to the surface is obtained in proportion to how high the AC power frequency supplied to the AC bridge circuit is, and information reflecting the state of residual stress in a region deep below the surface is obtained in proportion to how low the AC power frequency is. As in the claim 4 invention, setting a low frequency for the AC power supplied to the AC bridge circuit enables inspection of whether residual stress has been correctly imparted after the first shot peening, and setting a high frequency enables inspection of whether residual stress has been correctly imparted after the second shot peening. Combining these inspections makes it possible to judge whether the first shot peening and second shot peening have respectively been correctly performed, thus enabling more accurate inspection. It is also possible to judge in a manner distinguishing which of the shot peenings was incorrect.

In the invention of claim 5, a technical means is used whereby in the surface property inspection method of claim 4, the threshold value setting step determines the threshold value determined based on the output signal obtained by supplying a predetermined first frequency AC power to the AC bridge circuit, and a second threshold value determined based on the output signal obtained by supplying a predetermined second frequency AC power to the AC bridge circuit, the second frequency is higher than the first frequency and the threshold value is used to make a pass/fail judgment in the pass/fail judgment step and the second threshold value is used to make the pass/fail judgment in the second pass/fail judgment step.

Using the invention of claim 5, the (first) threshold value used for inspection of the first shot peening and the second threshold value used for inspection of the second shot peening are respectively set according to the frequency used for inspection, therefore an accurate judgment can be made as to whether the first shot peening and second shot peening were correctly performed.

In the invention of claim 6, a technical means is used in the surface property inspection method of claim 4 whereby the second pass/fail judgment step is performed before the pass/fail judgment step.

Since the response speed of the output value at the time of inspection is faster with a higher frequency, as the invention recited in claim 6, to previously perform the inspection of the second shot peening, in which the supplied AC power has a higher frequency, enables the time required for inspection to be shortened.

In the invention of claim 7, a technical means is used in the surface property inspection methods of claim 3 or claim 5 whereby in the threshold value setting step, by using an output signal EA from the AC bridge circuit when an untreated test object is disposed in the inspection detector, and an output signal EB from the AC bridge circuit when the test object on which the first shot peening and the second shot peening have been correctly performed is disposed in the inspection detector, the threshold value Ethi is determined according to the expression:

$$Ethi=(EAav \cdot \sigma B + EBav \cdot \sigma A)/(\sigma A + \sigma B),$$

where EAav: average value of the output signal EA; EBav: average value of the output signal EB; σA: standard deviation in the output signal EA; σB: standard deviation in the output signal EB.

Using the invention of claim 7, an appropriate initial threshold value can be set with high accuracy using a small number of measurement iterations.

In the invention of claim 8, a technical means is used in the surface property inspection methods of any one of claims 1 through 7 whereby the evaluation device comprises a memory device by which identifying information for each test object, and surface property inspection data for said test object, are correlated and stored.

Using the invention of claim 8, identifying information for each test object such as lot, manufacturing number, history, and the like can be correlated and stored with measurement values, pass/fail judgment results, measurement data and time, inspection conditions, etc., therefore the surface treatment state of a test object inspected by a surface property inspection apparatus can be traced after distribution, thereby assuring traceability.

The invention of claim 9 uses a technical means, being a surface property inspection apparatus for inspecting a surface property of a test object subjected to a first shot peening for imparting residual stress from a surface into deep portions by a shot peening apparatus, and a second shot peening for performing, after the first shot peening, a lower strength shot peening than the first shot peening, thereby imparting further residual stress close to the surface, the apparatus comprising: an AC bridge circuit; an AC power supply for supplying AC power to the AC bridge circuit; and an evaluation device for evaluating the surface property of the test object based on an output signal from the AC bridge circuit; wherein the AC bridge circuit comprises: a variable resistor in which the distribution ratio can be varied between a first resistor and a second resistor, an inspection detector comprising a coil capable of exciting AC magnetism, formed so that said coil can be disposed to excite an eddy current in the test object, and a reference detector in which a reference test object having the same structure as the test object is disposed, and detecting a reference state which serves as a reference for comparison with an output from the inspection detector; wherein the first resistor, the second resistor, and the reference detector and the inspection detector constitute the bridge circuit, and wherein the evaluation device evaluates the surface property of the test object to judge whether the first shot peening has been properly performed on the test object only after the second shot peening by comparing a threshold value and the output signal from the AC bridge circuit in a state that AC power is supplied to the AC bridge circuit, the inspection detector detects electromagnetic property of the test object, and the reference detector detects the reference state.

Using the invention of claim 9, an eddy current can be excited in a test object by an inspection detector coil, and the surface properties of the test object can be evaluated by comparing the output signal output from an AC bridge circuit to a threshold value. This enables high precision inspection of the surface state using a simple circuit configuration. Also, a method is adopted in which an eddy current is excited in the test object to inspect surface properties, therefore the effects of temperature variations on the inspection environment can be reduced.

Because a reference test object of the same structure as the test object is used to detect a reference state in a reference detector, fluctuations in output values due to changes in the inspection environment such as temperature, humidity, and magnetism will be the same as in the test object Fluctuations in output values caused by changes in the inspection environment such as temperature, humidity, or magnetism can thus be canceled and measurement accuracy improved.

By inspecting the surface properties of a test object subjected to a two stage shot peening comprising a first shot peening and a second shot peening only after the second shot peening, an inspection can be made of whether residual stress has been correctly imparted over a range, for example, of approximately 30-100 μm from the surface, to judge the quality of the first shot peening. By so doing, a judgment of whether the second stage peening has been correctly performed can be made by a single inspection after performing the two stage shot peening, thereby shortening inspection time. Inspection can also be quickly and non-destructively performed, making this method suitable for inline inspection, as well.

In the invention of claim 10, a technical means is used in the claim 9 surface property inspection apparatus whereby the reference test object is an untreated object not subjected to surface treatment.

As in the claim 10 invention, when an untreated object not subjected to surface treatment is used as a reference test object, the output based on the difference between the surface state of the reference test object and the test object can be increased, measurement accuracy can be further improved, and the threshold value more easily set, making this preferable.

The claim 11 invention uses a technical means whereby the coil in the surface property inspection apparatus of claim 9 or 10 is formed of Litz wire.

In the claim 11 invention, the coil is formed using a Litz wire in which fine conducting strands of copper wire or the like are insulated by covering with enamel or the like and collected and twisted together as multiple fine conductor strands, therefore the conductor surface area can be enlarged by refining the conductors, thereby reducing conductor losses and enabling a favorable inspection sensitivity to be maintained.

BRIEF DESCRIPTION OF FIGURES

FIG. 6(A) is an explanatory diagram showing changes in output value from placement of a test object through start of measurement.

FIG. 6(B) is an explanatory diagram showing changes in output values from the measurement completion through removal of the test object.

FIG. 8 is a flowchart showing a surface property inspection method in a second embodiment.

FIG. 9(A) is an explanatory diagram showing the change in output values from placement until completion of measurement of a test object in the second embodiment surface property inspection apparatus, and is an explanatory diagram showing changes in output values when a first shot peening inspection step is performed after a second shot peening inspection step is performed.

FIG. 9(B) is an explanatory diagram showing the change in output values from placement until completion of measurement of a test object in the second embodiment surface property inspection apparatus, and is an explanatory diagram showing changes in output values when a second shot peening inspection step is performed after a first shot peening inspection step is performed.

DETAILED DESCRIPTION OF THE PREFERRED EMBODIMENTS

First Embodiment

Two Stage Shot Peening

In the present invention the surface treatment to which the test object inspected for surface properties is subjected consists of a first shot peening using a relatively high strength shot peening for imparting residual stress from the surface down to a region of a predetermined depth or greater (the "deep portion" below), and a second shot peening for imparting further residual stress near the surface by shot peening at a lower strength than the first shot peening. Below we explain the case in which two stages of shot peening are applied to a gear G as the treated material.

Here the first shot peening and second shot peening are performed using a known shot peening apparatus, such as a shot peening apparatus comprising a direct pressure air nozzle.

In the first shot peening, compressive residual stress is imparted down to a deep portion, e.g., a depth of approximately 30 μm to 100 μm from the surface.

The first shot peening is conducted by causing a projection material (shot) with a relatively large particle size and high hardness to collide with the treated material.

Steel or the like selected from a range of Vickers hardness of HV500 to HV850 and a particle size of 0.5 to 4.0 mm may be used for the projection material. If a direct pressure shot peening apparatus is used, for example, a projection pressure of 0.05 to 0.7 MPa and a 20 kg/min nozzle maximum projection quantity may be used as the projection parameters. The numerical value of the Vickers hardness is measured by the test method set forth in JIS Z2244 (2009).

For example, using a projection material particle size of 0.6 mm and hardness HV580, shot peening can be performed at a projection pressure of 0.3 MPa, projection quantity of 13 kg/min, and projection time of 10 seconds.

In the second shot peening, shot peening is performed using a smaller projection material than in the first shot peening, and residual stress is further imparted close to the surface, for example at a depth of approximately 30 μm from the surface.

Projection material used in the second shot peening is a smaller projection material than that used in the first shot peening; the projection material can be appropriately selected from steel or the like in a Vickers hardness range of HV500 to HV1200 and a particle size range of 0.05 to 0.5 mm.

If a direct pressure shot peening apparatus is used, for example, a projection pressure of 0.05 to 0.7 MPa and 20 kg/min maximum projection quantity may be used as the projection conditions. Since the projection material used for the second shot peening is smaller than the projection material used for the first shot peening, the second shot peening is a lower strength shot peening than the first shot peening.

For example, using a projection material particle size of 0.05 mm and hardness of HV900, shot peening can be performed at a projection pressure of 0.2 MPa, projection quantity of 10 kg/min, and projection time of 10 seconds.

(Surface Property Inspection Apparatus)

Figure 1A:
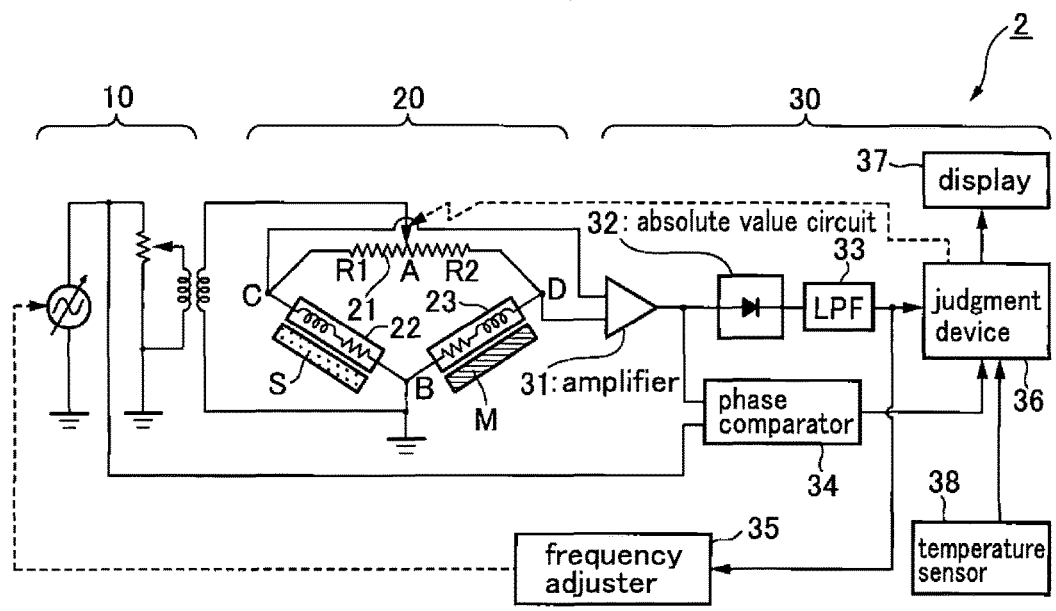
FIG. 1(A) is an explanatory drawing showing the circuit structure of a surface property inspection apparatus.

As shown in FIG. 1(A), a surface property inspection apparatus 1 according to an embodiment of the present invention comprises a shot peening apparatus 10, an AC bridge circuit 20, and an evaluation device 30.

The AC power supply 10 is capable of supplying AC power at a variable frequency to the AC bridge circuit 20.

The AC bridge circuit 20 comprises a variable resistor 21, a reference detector 22, an inspection detector 23 formed to permit disposition of a coil to excite an eddy current in test object M, and a reference detector 22, formed to permit disposition of reference test object S of the same structure as test object M, for detecting the reference state serving as the reference for comparison with the output from inspection detector 23. Here the word "same structure as the test object M" means the same materials and shape, regardless of whether or not subjected to surface treatment.

A variable resistor 21 is constituted so as to variably distribute the distribution ratio γ of a resistor RA into resistance R1 and resistance R2. The resistor R1 and resistor R2, together with the reference detector 22 and the inspection detector 23, constitute a bridge circuit. In the present embodiment, point A dividing the resistor R1 and resistor R2, and point B between the reference detector 22 and the inspection detector 23, are connected to the AC power supply 10 in the evaluation device 30, and point C between the resistor R1 and the reference detector 22 and point D between the resistor R2 and the inspection detector 23 are connected to the amplifier 31. To reduce noise, the reference detector 22 and the inspection detector 23 sides are grounded.

The evaluation device 30 is furnished with an amplifier 31 for amplifying a voltage signal output from the AC bridge circuit 20, an absolute value circuit 32, a low-pass filter (LPF) 33, a phase comparator 34 for comparing the phases between the AC voltage supplied from AC power supply 10 and the voltage output from amplifier 31, a frequency adjuster 35 for adjusting the frequency of the AC voltage supplied from the AC power supply 10, a judgment means for performing a non-equilibrium adjustment to optimize the distribution between R1 and R2 and judge a pass/fail state of the surface of the test object M based on the output from LPF 33, a display means 37 for displaying and warning the judgment results by judgment means 36, and a temperature measurement means 38 for detecting the temperature at the evaluation position. A memory device is also furnished, either inside the judgment means 36 or in an area not shown.

Amplifier 31 is connected to points C and D and receives an input of the potential difference between point C and point D. The absolute value circuit 32 and the LPF 33 are connected in that order to the judgment means 36. The phase comparator 34 is connected to the AC power supply 10, the amplifier 31, and the judgment means 36. The frequency adjuster 35 is connected to the AC power supply 10 and the amplifier 31. The judgment means 36, by outputting a control signal, can change the position of point A in the AC bridge circuit 20, i.e., it can change the distribution ratio γ between the resistor R1 and the resistor R2; thus executing the variable resistance setting step described below.

The temperature measurement means 38 comprises a non-contacting infrared sensor or thermocouple, and outputs a temperature signal for the surface of the test object M to the judgment means 36. When the temperature of the test object M detected by the temperature measurement means 38 is within a predetermined range, the judgment means 36 makes a pass/fail judgment of the surface treatment state of the test object M; when the temperature detected by the temperature measurement means 38 is outside a predetermined range, no pass/fail judgment is made of the surface treatment state of the test object M. This makes it possible not to perform a pass/fail judgment of the surface treatment state of the test object when the temperature of the test object M is affecting the accuracy of the inspection, thus enabling a high accuracy inspection to be performed. Here the evaluation position Ts may be measured by a thermocouple or the like, and a judgment made as to whether or not to make a pass/fail judgment of the surface property state of the test object M as a representative temperature for the temperature of the test object M.

As the inspection detector 23 and reference detector 22 of the same constitution as the inspection detector 23, a detector is used in which a coil is formed by winding around a core into which the evaluation portion of the test object M can be inserted, and the coil is placed opposite the test object M surface and brought into proximity to excite eddy currents in the test object M. That is, the coil is wound to surround and oppose the surface property inspection area of the test object. Here, "surround the surface property inspection area of the test object" includes the meaning of exciting an eddy current in the surface property inspection area by enveloping (wrapping around) at least a portion of the surface property inspection area.

Figure 1B:
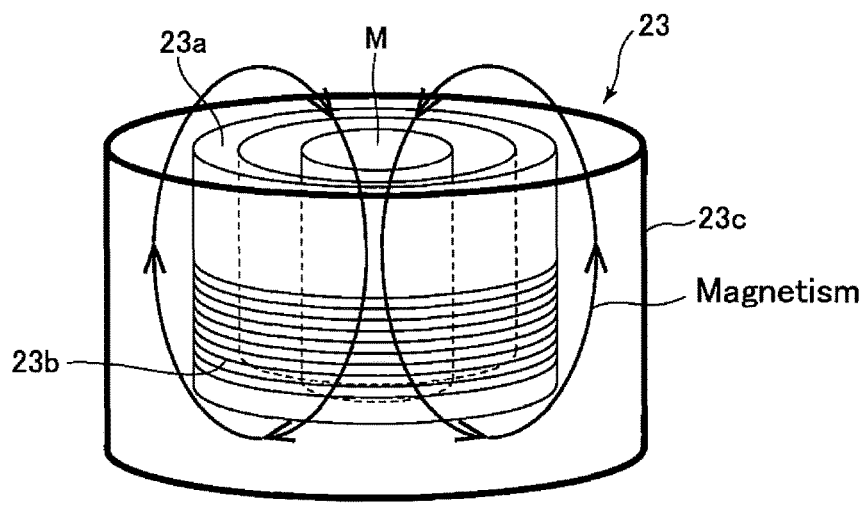
FIG. 1(B) is a perspective explanatory diagram showing the structure of an inspection detector.

Here we explain an inspection detector 23 used to inspect the surface properties of a test object comprising a gear portion as the test object M, such as the surface properties of a gear G in which the gear portion is surface treated. The inspection detector 23, as shown in FIG. 1(B), comprises a cylindrical core 23a formed to cover the gear portion of the gear G, and a coil 23b wound around the exterior perimeter surface of the core 23a. The core 23a is formed of a non-magnetic material, for example resin. Note that the shape of the core 23a is not limited to a cylinder so long as the gear G can be disposed within it. Note also that a reference test object S for outputting a reference output may be placed without placing a test object M.

The inspection detector 23 has the feature that it captures eddy current reactions with high accuracy when evaluating surface properties, therefore it should preferably be disposed relative to test object M so that eddy currents flow in the region in which one wishes to inspect surface properties. That is, it is preferable for the direction of windings in the coil 23b to be disposed in the same direction as the direction in which one wishes eddy currents to flow.

A residual stress layer is formed in the gear portion by shot peening the gear G. When evaluating the gear G as a test object M, it is preferable to evaluate the surface properties of not only tooth tips, but also tooth surfaces and tooth bottoms. To do this, the winding direction of the coil 23b is disposed essentially perpendicular to the rotational axis of the gear G. Since a magnetic loop is generated in the rotational direction, this enables an eddy current to be excited in the rotational direction of the gear G, so that not only the tooth tip, but also the tooth surface and tooth bottom can be evaluated. Conventional contacting detectors required multiple types of detector to be prepared to fit the shape of the tooth being inspected, and surface properties close to the contacting portion could not be inspected, but using the inspection detector 23, a broad range of surface properties can be inspected at once with a single detector.

The inspection detector 23 does not have to comprise a core 23a so long as the coil 23b can maintain its shape. Such a coil 23b may be formed, for example, by adhesion of an enamel copper wire wound on an air core using a hardening epoxy resin or the like, or by winding around an air core using a fusing enamel copper wire with a heat-hardening action, then hardening with heat from hot air or a drying oven.

The inspection detector 23 is disposed so that the coil 23b opposes and surrounds the surface to be inspected of the test object M; an AC magnetic field is generated when AC power at a predetermined frequency is supplied to the coil 23b by the AC power supply 10, and an eddy current flowing in a direction intersecting the AC magnetic field is excited on the surface of the test object M. Since eddy currents change in response to electromagnetic properties of the residual stress layer, the phase and amplitude (impedance) of the output waveform output from amplifier 31 changes in response to properties of the residual stress layer (the surface treatment state). Electromagnetic properties of the surface treatment layer can be detected using these changes in output waveform to perform an inspection.

It is also possible to provide a magnetic shield 23c disposed outside the inspection detector 23 and surrounding the test object M. By using a magnetic shield 23c, external magnetism can be blocked, therefore false detections can be prevented.

(Output from the AC Bridge Circuit)

Figure 2:
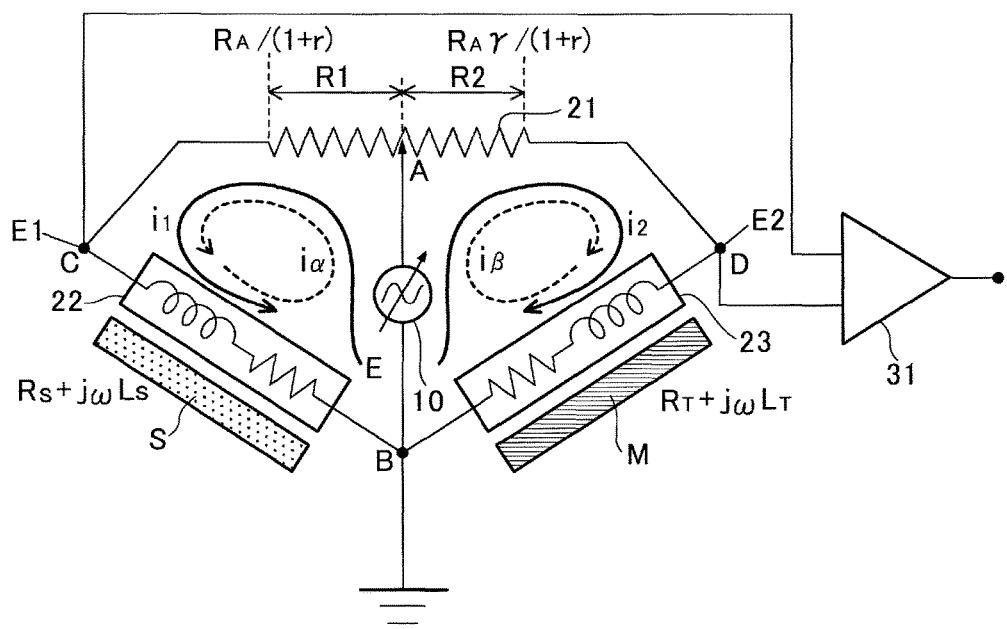
FIG. 2 is an equivalent circuit diagram explaining the output from an AC bridge circuit.

Next, referring to the equivalent circuit in FIG. 2, we explain the output from AC bridge circuit 20, adjusted to a non-equilibrium state. A reference test object S for outputting a reference output is placed in close proximity to the reference detector 22, and the test object M for which a pass/fail determination of the surface treatment state is required is placed in close proximity to the inspection detector 23.

Here the reference test object S has the same structure as the test object M, and preferably uses an untreated part on which no surface treatment has been performed.

Assuming a distribution ratio for variable resistor $R_A$ of $\gamma$, resistor R1 is $R_A/(1+\gamma)$, and resistor R2 is $R_A\gamma/(1+\gamma)$. The reference detector 22 impedance is assumed to be $R_S+j\omega L_S$, and the impedance of the inspection detector 23 is assumed to be $R_T+j\omega L_T$. We assume a potential E at point A, respective excitation currents $i_1$, $i_2$ flowing at each side of the bridge when each of the test objects (reference test object S, test object M) is not placed in proximity to the reference detector 22 or the inspection detector 23, and respective currents $i\alpha$ and $i\beta$ flowing in response to the amount of change in magnetism when each test object is brought into proximity with the reference detector 22 and the inspection detector 23. The potentials E1 and E2 and excitation currents $i_1$ and $i_2$ on the reference detector 22 and the inspection detector 23 in this instance are expressed by Expressions (1) through (4) below.

Exp. 1
$$E1 = (R_s + j\omega L_S)(i\alpha + i_1) \tag{1}$$

Exp. 2
$$E2 = (R_T + j\omega L_T)(i\beta + i_2) \tag{2}$$

Exp. 3
$$i_1 = \frac{E}{\frac{R_A}{1+\gamma} + R_S + j\omega L_S} \tag{3}$$

Exp. 4
$$i_2 = \frac{E}{\frac{R_A\gamma}{1+\gamma} + R_T + j\omega L_T} \tag{4}$$

The voltage output at the amplifier 31 is the difference between E1 and E2, and is expressed as follows.

Exp. 5:

$$E2-E1=[\{(R_T+j\omega L_T)i\beta-(R_S+j\omega L_S)i\alpha\}+\{(R_T+j\omega L_T)i_2-(R_S\pm j\omega L_S)i_1\}] \quad (5)$$

The following expression is derived from Expressions (3) through (5).

Exp. 6

$$E2 - E1 = \left[ \{(R_T + j\omega L_T)i\beta - (R_S + j\omega L_S)i\alpha\} + \left\{ (R_T + j\omega L_T)\dfrac{E}{\dfrac{R_A\gamma}{1+\gamma} + R_T + j\omega L_T} - (R_S + j\omega L_S)\dfrac{E}{\dfrac{R_A}{1+\gamma} + R_S + j\omega L_S} \right\} \right] \quad (6)$$

We now divide the right side of Exp. (6) into the following Components A and B, and consider the various components of the differential voltage.

$$(R_T + j\omega L_T)i\beta - (R_S + j\omega L_S)i\alpha \quad \text{Component A}$$

$$(R_T + j\omega L_T)\dfrac{E}{\dfrac{R_A\gamma}{1+\gamma} + R_T + j\omega L_T} - (R_S + j\omega L_S)\dfrac{E}{\dfrac{R_A}{1+\gamma} + R_S + j\omega L_S} \quad \text{Component B}$$

Component A comprises each of the detector components: $(R_S+j\omega L_S)$, $(R_T+j\omega L_T)$, and the electrical current amounts $i\alpha$ and $i\beta$, which change when each of the test objects is placed in proximity to each detector. The sizes of $i\alpha$ and $i\beta$ vary with the amount of magnetism passing through the test object due to electromagnetic properties such as magnetic permeability and electrical conductivity. It is therefore possible to change $i\alpha$ and $i\beta$ by changing the excitation currents $i_1$, $i_2$ which control the amount of magnetism produced by each detector. It can also be seen from Expressions (3) and (4) that excitation currents $i_1$ and $i_2$ change depending on the variable resistor distribution ratio $\gamma$, therefore the size of Component A can be changed by adjusting the variable resistor distribution ratio $\gamma$.

Component B comprises each of the detector components: $(R_S+j\omega L_S)$, $(R_T+j\omega L_T)$, and the resistance parameter divided by the variable resistor distribution ratio $\gamma$. Therefore the size of Component B can be changed by adjusting the variable resistor distribution ratio $\gamma$ in the same way as for Component A.

When test object M is disposed at a predetermined position and AC power at a predetermined frequency is supplied to the inspection detector 23 coil 23b by the AC power supply 10, an eddy current flowing in a direction crossing the AC magnetic field is excited on the surface of test object M. Since eddy currents change in response to electromagnetic properties of the residual stress layer, the phase and amplitude (impedance) of the output waveform (voltage waveform) output from the amplifier 31 change in response to properties of the residual stress layer (the surface treatment state). Electromagnetic properties of the residual stress layer can be detected using these changes in output waveform to perform an inspection of the surface treatment layer.

Signals output from the bridge amplifier 31 are signals which extract the differential surface area between the reference detector 22 and inspection detector 23 voltage waveforms and form a circuit for holding fixed the current flowing in the detector (excitation current). The extracted voltage signal can also be thought of as a power signal.

Power supplied to the detector is always constant. Magnetic energy supplied to the test object M can in this way be kept constant.

(Surface Property Inspection Method)

Figure 3:
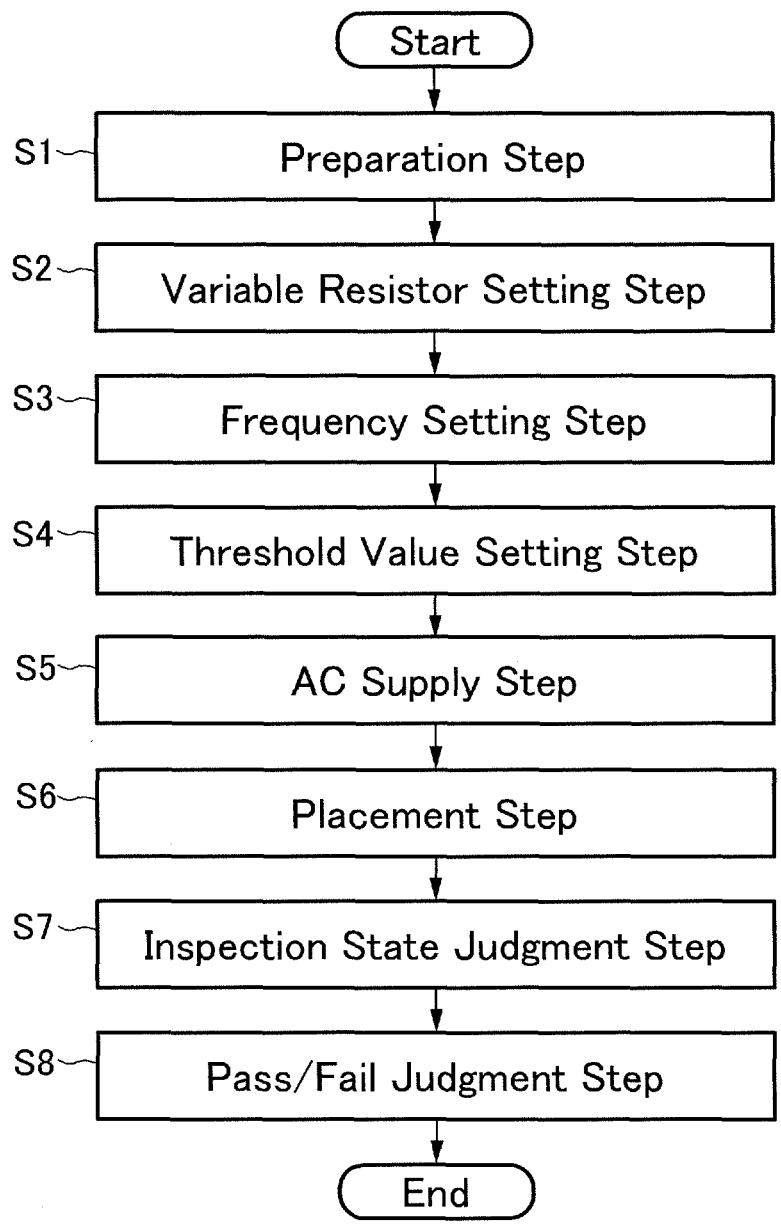
FIG. 3 is a flowchart showing a surface property inspection method.

Next, referring to FIG. 3, we explain a test object surface property inspection method using surface property inspection apparatus 1.

First, the surface property inspection apparatus 1 and a reference test object S are prepared in preparatory step S1, which is an inspection apparatus preparation step.

Next, a variable resistor setting step S2 is performed. In variable resistor setting step S2, AC power is first supplied from the AC power supply 10 to the AC bridge circuit 20. In this state, the distribution ratio $\gamma$ of the variable resistor 21 is adjusted to achieve a high test object detection accuracy by the surface property inspection apparatus 1. That is, the distribution ratio $\gamma$ of the variable resistor 21 is adjusted so that the output signal of the AC bridge circuit 20 is reduced without placing the test object in proximity to the inspection detector 23. By thus setting the variable resistor 21, the difference in output signal is increased between the case when the surface treatment state of a test object M brought into proximity with the inspection detector 23 is poor, and the case when the surface treatment state is good, and detection accuracy can be raised. Specifically, the voltage amplitude of the output signal from the AC bridge circuit 20 or the voltage output from the LPF 33 are monitored using a display device with a waveform display function such as an oscilloscope (e.g., the one comprising judgment means 36), and the distribution ratio $\gamma$ is adjusted so that output diminishes. The distribution ratio $\gamma$ of the variable resistor 21 is preferably adjusted and set so that the output reaches a minimum value or a local minimum value (local equilibrium point).

Adjustment of the variable resistor 21 distribution ratio $\gamma$ is performed in order to improve inspection accuracy by increasing the output difference corresponding to the difference in surface states by reducing the differential voltage (E2−E1). As described above, Components A and B are changed by adjusting the distribution ratio $\gamma$, therefore the variable resistor 21 distribution ratio $\gamma$ can be adjusted in response to the impedance $(R_S+j\omega L_S)$ and $(R_T+j\omega L_T)$ of the reference detector 22 and the inspection detector 23, and the differential voltage (E2−E1), which is the output from AC bridge circuit 20, can be reduced. Thus the difference in properties between the reference detector 22 and the inspection detector 23 can be reduced, and at least a little more of the inherent properties of the test object M can be extracted, improving detection accuracy.

In frequency setting step S3, AC power is supplied from the AC power supply 10 to the AC bridge circuit 20 with reference test object S brought into proximity with inspection detector 22, the frequency of AC power supplied to AC bridge circuit 20 by frequency adjuster 35 is varied, and the voltage amplitude output from AC bridge circuit 20 or the voltage output from LPF 33 are monitored.

Frequency adjuster 35 outputs a control signal to AC power supply 10 to achieve the initial frequency f1 set in frequency adjuster 35, and the output voltage Ef1 from amplifier 31 at frequency f1 is input to frequency adjuster 35 and stored. Next, a control signal is output to the AC power supply 10 to reach a frequency f2, which is higher than frequency f1 by a predetermined value, such as 100 Hz; an output voltage Ef2 from the amplifier 31 at frequency f2 is input to the frequency adjuster 35 and stored.

Next, a comparison is made between Ef1 and Ef2; if Ef2>Ef1, a control signal is output so as to reach a frequency f3 higher by a predetermined value than frequency f2; an output voltage Ef3 from amplifier 31 at frequency f3 is input to frequency adjuster 35 and stored. Ef2 and Ef3 are then compared. This is repeated, and the frequency fn when Efn+1<Efn, i.e. the frequency fn at which output is maximum, is set as the frequency used in the frequency setting step S4 and the AC supply step S5. This enables setting of a frequency by a one-time operation to cause the output from the AC bridge circuit 20 to increase in response to objects under test M with differing surface treatment states or shapes and differing impedances. Optimal frequency changes depending on the material, shape, and surface treatment state of the test object, but when these are known in advance, setting the frequency is unnecessary. Thus a sensitive response to changes in the surface treatment state is possible, and inspection sensitivity can be improved.

Here, frequency setting step S3 can also be executed before variable resistor setting step S2.

Figure 4:
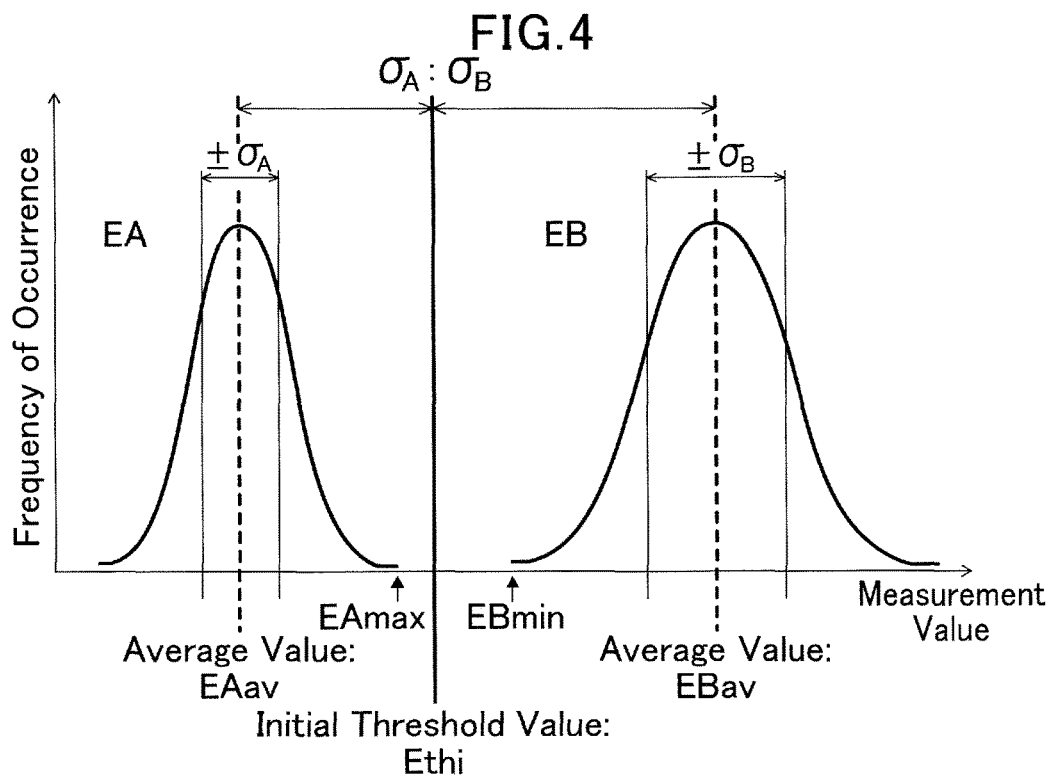
FIG. 4 is a diagram explaining a method for setting an initial threshold value.

In the threshold value setting step S4, the threshold value used to judge the quality of the test object M surface state is set. Here we explain a method for pre-setting the threshold value ("initial threshold value" below) for use at the start of evaluation of a test object M. First, the reference test object S is placed in proximity to the reference detector 22, and AC power at a frequency set in the frequency setting step S3 is supplied from the AC power supply 10 to the AC bridge circuit 20. The voltage output from the AC bridge circuit 20 is amplified by the amplifier 31; full wave rectification is performed by the absolute value circuit 32; a DC conversion is performed in the LPF 33, and the result is output to the judgment means 36. Of the untreated units under test and the units under test treated by two stage peening, approximately 10 to several 10s of pieces judged to be good product, on which first shot peening and second shot peening have both been correctly performed, are prepared, and output value distribution data is acquired from the output values output to the judgment means 36 when the respective test objects are placed in proximity to the inspection detector 23. This is shown schematically in FIG. 4.

The initial threshold value Ethi is determined by the following expression, with consideration for the variability of the respective output signals, based on the output signal EA when an untreated test object M is placed in the inspection detector 23, and on the output EB when a treated test object M from a good part is placed in the inspection detector 23. The distribution between output signal EA from the untreated test object and output signal EB from the treated test object is shown schematically in FIG. 4.

$$Ethi=(EA_{av}\cdot\sigma B+EB_{av}\cdot\sigma A)/(\sigma A+\sigma B),\quad \text{Exp. 7:}$$

where EAav: average value of the output signal EA; EBav: average value of the output signal EB; σA: standard deviation in the output signal EA; σB: standard deviation in the output signal EB.

A high accuracy appropriate threshold value can thus be set with a small number of measurements. This initial value Ethi is set as an initial value and stored in the judgment means 36. Here the initial threshold value Ethi has the relationship EAmax<Ethi<Ebmin between the maximum value EAmax of the output signal EA and the minimum value EBmin of the output signal EB.

Note that even when the relationship above is not satisfied, an appropriate initial threshold value Ethi can be set by taking into account factors such as variability in the output signal EA and output signal EB, and whether there are unique measurement values greatly divergent from the distribution, etc. For example, there is a method whereby multiple measurements are performed on the untreated state and the surface treated state of the same units under test, and using the initial threshold value Ethi is re-computed.

When an appropriate threshold value is already known, that value may be adopted.

In addition, in threshold value setting step S4 an output signal with the test object M not in proximity to the inspection detector 23 is stored in the judgment means 36 as initial offset value Ei.

In AC supply step S5, AC power at the frequency set in frequency setting step S3 is supplied from AC power supply 10 to AC bridge circuit 20. Here the reference test object S is proximate to the reference detector 22.

Next, in disposition step S6, the test object M for which a determination of pass/fail for the surface processing state is to be made is brought into proximity with inspection detector 23 and an eddy current is excited in the test object. Therefore the AC supply step S5 and the disposition step S6 function as an eddy current excitation step. At this point a voltage output signal is output from the AC bridge circuit 20; the output signal is amplified by the amplifier 31, full wave-rectified by the absolute value circuit 32, and converted to DC by the LPF 33.

Before test object M approaches inspection detector 23, or after disposition of test object M, the temperature measure means 38 measures the surface temperature of test object M, and outputs a test object M surface temperature signal to judgment means 36.

In test state judgment step S7, a comparison is made by phase comparator 34 between the AC power waveform supplied from AC power supply 10 and the AC voltage waveform output from AC bridge circuit 20, and their phase differences are detected. By monitoring this phase difference, a judgment can be made as to whether or not the inspection state is good (e.g., there is no positional offset between the inspection detector 23 and the test object M). Even if the outputs from the AC bridge circuits 20 are the same, the inspection state changes when there are large changes in phase difference, and a judgment can be made that the inspection may not be being correctly implemented. In addition, when the temperature of the test object M detected by the temperature measurement means 38 is within a predetermined range, the judgment means 36 makes a pass/fail judgment of the test object M surface treatment state; when the temperature detected by temperature measurement means 38 is outside a predetermined range, no pass/fail judgment is made of the surface treatment state of the test object M. Here the predetermined temperature range is the temperature range in which changes in the test object M temperature exert no substantive effect on the inspection; it can be set, for example, to 0 to 60° C. Various measures can be undertaken when the temperature of the surface of test object M is outside a predetermined temperature range, such as placing the system in standby, or blowing air onto the test object M, or moving the test object M to a different line without testing it, until the test object M falls within a predetermined temperature range.

In pass/fail judgment step S8, the signal converted to DC by LPF 33 is input to judgment means 36; judgment means 36 judges the pass/fail state of the surface of test object M based on the inputted signal.

That is, this step is an evaluation step for evaluating the surface properties of a test object M based on an output signal from the AC bridge circuit 20. The judgment results by the judgment means 36 are displayed by the display means 37, and if the surface state is poor (if the first shot peening is not correctly implemented), a warning is issued.

The judgment of the test object M surface processing pass/fail state is carried out by comparing the output value (measurement value) from LPF 33 with the threshold value set in threshold value setting step S4. If the output value (measured value) from the LPF 33 exceeds the threshold value, the judgment means 36 judges that the surface state is good (the first shot peening is correctly implemented); if the output value (measured value) from the LPF 33 is below the threshold value, the judgment means 36 judges that the surface state is poor (the first shot peening is not correctly implemented). Note that "whether the first shot peening has been correctly performed" is a concept which includes the quality of the first shot peening as well as whether the first shot peening has been implemented.

Inspection data such as measured value, pass/fail judgment result, date of measurement, and inspection state (temperature, humidity, differential voltage ΔE described below, etc.) are correlated with lot, production number, history, or other information identifying each test object M and stored in the evaluation apparatus 30 judgment means 36 or in a memory device not shown. That is, identifying marks associated with each of the measurement data can be directly or indirectly appended to the test object. For example, a bar code or product control number associated with measurement data can be directly or indirectly displayed. By associating measurement data in this way to identifying markings such as bar codes, product control numbers, etc., the surface state of a test object inspected by a surface property inspection apparatus can be tracked after distribution, thereby assuring traceability.

Through the above-described steps, by inspecting the surface properties of a test object subjected to a two stage shot peening comprising a first shot peening and a second shot peening only after the second shot peening, an inspection can be made of whether residual stress has been correctly imparted over a range, for example, of approximately 30-100 μm from the surface, to judge the quality of the first shot peening. By so doing, a judgment of whether the second stage peening has been correctly performed can be made by a single inspection after performing the two stage shot peening, thereby shortening inspection time. Inspection can also be quickly and non-destructively performed, making this method suitable for inline inspection, as well.

To continue the test, it is sufficient to swap only the test object M and repeat placement step S6, test state judgment step S7, and pass/fail judgment step S8. If the type of test object M or the type of surface treatment etc. is changed, variable resistor setting step S2, frequency setting step S3, and threshold value setting step S4 are again performed.

The inspection detector 23, by capturing changes in the eddy current flowing on the surface of a test object M, can indirectly capture changes in surface resistance. That is, detection is made of whether shot peening has been correctly performed and whether the desired residual stress has been imparted by detecting changes in the conductivity and magnetic permeability of the test object M. Here, this surface property inspection method enables the penetration depth of eddy currents to be changed by changing the frequency of the AC power, therefore surface properties can be inspected down to a desired depth from the surface, and the method can be favorably used to inspect whether residual stress has been correctly imparted.

Since a reference test object S including a reference detector 22 of the same structure as the test object M, which includes the inspection detector 23, is used to detect the reference state in the reference detector 22, fluctuations in output values due to changes in the inspection environment such as temperature, humidity, magnetism, are equal to those occurring in the test object M including the inspection detector 23. Fluctuations in output values caused by changes in the inspection environment such as temperature, humidity, or magnetism can thus be canceled and measurement accuracy improved. In particular, use of an untreated part on which no surface treatment has been performed as the reference test object S enables the output, which is based on the difference in surface state relative to the test object M, to be increased, therefore measurement accuracy can be still further improved and the threshold value more easily set, which is preferable.

(Threshold Value Update Setting)

If there is a large difference between the output signal EA when an untreated test object M is placed in the inspection detector 23 and the output signal EB when a surface treated test object M with a good surface state is placed in the inspection detector 23, the initial threshold value Ethi may approach the average value EAav side of the output signal EA, broadening the range of the output deemed to indicate good product. Therefore if one wishes to set a still more accurate threshold value, the threshold value can be reset based on a large amount of inspection data accumulated by repeated measurements using the initial threshold value Ethi. The newly set threshold value in this instance is referred to as updated threshold value Ethn.

Setting of the updated threshold value Ethn is performed after inspecting 100 or more test objects M. An example of the method for setting an updated threshold value Ethn is shown below. Here the output signal from a test object M inspected using an initial threshold value Ethi shall be EC; the minimum value thereof shall be ECmin, the maximum value ECmax, the average value ECav, and the standard deviation σC.

In one method, the initial threshold value Ethi and minimum value ECmin are compared, and the updated threshold value Ethn is calculated as follows.

If ECmin≤Ethi, the initial threshold value Ethi is used without setting the updated threshold value Ethn.

If ECmin>Ethi, the ECmin can be set as the updated threshold value Ethn.

It is also possible, using average value ECav and standard deviation σC, to adopt ECav-3σC or ECav-4σC for the updated threshold value Ethn. Which of ECav-3σC or ECav-4σC to use should be judged with consideration for the distribution of the output signal EC; when ECav-3σC or ECav-4σC is equal to or less than the initial threshold value Ethi, the initial threshold value Ethi is used without setting an updated threshold value Ethn.

An updated threshold value Ethn can also be set based on the relative sizes of the minimum value ECmin, maximum value ECmax, and average value ECav. Specifically, cases are distinguished by comparing the average value of minimum value ECmin and maximum value ECmax (ECmin+ECmax)/2 with the average value ECav.

If (ECmin+ECmax)/2≤ECav: set ECav-3σC as updated threshold value Ethn.

If (ECmin+ECmax)/2>ECav: set ECav-4σC as updated threshold value Ethn.

Here, if ECav-3σC or ECav-4σC is equal to or less than the initial threshold value Ethi, the initial threshold value Ethi is used without setting an updated threshold value Ethn.

The updated threshold value Ethn can be repeatedly updated based on inspection data for test objects M inspected after an update. For example, inspection of 100 test objects M could be performed after setting the initial threshold value Ethi, then inspection of a further 100 test objects M performed after setting updated threshold value Ethn, then a new updated threshold value Ethn set based on that inspection data. A new updated threshold value Ethn could also be set using inspection data for all 200 units.

(Measurement Calibration)

Measurements can be calibrated using the aforementioned initial offset value Ei and inspection offset value Eik.

Figure 5:
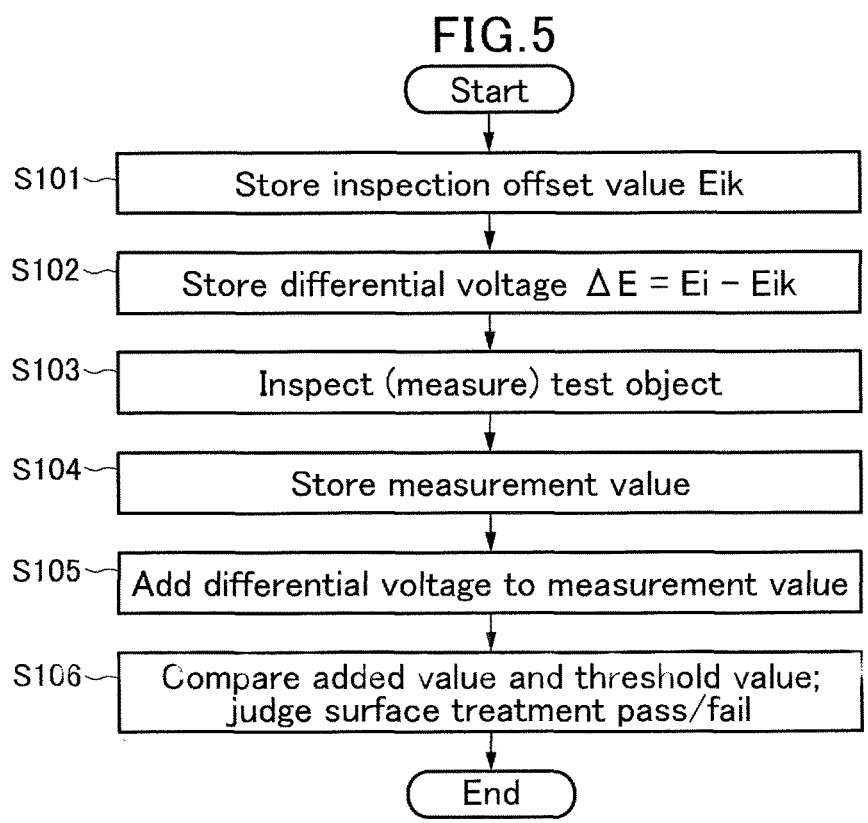
FIG. 5 is a flowchart showing a measurement value calibration method.

As shown in FIG. 5, in step S101 the inspection offset value Eik is measured and stored in the judgment means 36 before placement of a test object M in step S6.

In step S102 which follows, the initial offset value Ei and the inspection offset value Eik are compared and a differential voltage ΔE=Ei−Eik is calculated. Step S102 and beyond correspond to the pass/fail judgment step S8.

Inspection of the test object M is performed in step S103 and a measurement value (E2−E1) stored in step S104; differential voltage ΔE is added to the stored measurement value in step S105.

In step S106, the measurement value to which the differential voltage ΔE is added is compared to a threshold value to make a pass/fail judgment.

Thus even if the offset voltage changes due to changes in the measurement environment such as temperature, humidity, and magnetism, a high accuracy measurement, from which those effects are removed, can be performed. That is, an appropriately high accuracy measurement can be performed with calibration carried out each time on the measuring equipment (inspection apparatus).

If the differential voltage ΔE exceeds the allowable value set based on surface property inspection apparatus 1 usage conditions, a judgment can be made that the inspection state is inappropriate, such as when there are large disturbances or apparatus problems impeding correct performance of the inspection. In this case it is possible not to inspect the surface properties of the test object M in inspection state judgment step S7. On such occasions the reference detector 22 and inspection detector 23 may be checked, the temperature of the measurement environment confirmed, or the reference test object S checked or replaced, etc. Said allowable values can be set as conditions for appropriate performance of an inspection; for example, a setting of 5% of the initial offset value Ei (ΔE=0.05Ei) may be used.

(Control of Tested Piece Placement and Extraction)

The placement of the test object M in the inspection detector 23 and removal from the inspection detector 23 can be controlled using the measurement value En (En=E2−E1).

Referring to FIGS. 6 and 7, we now explain a method for controlling placement and removal of a test object. Note that FIG. 6 shows an example to explain the initial offset value Ei0 and output value En, and is shown schematically, so is not an actual output value.

Figure 7A:
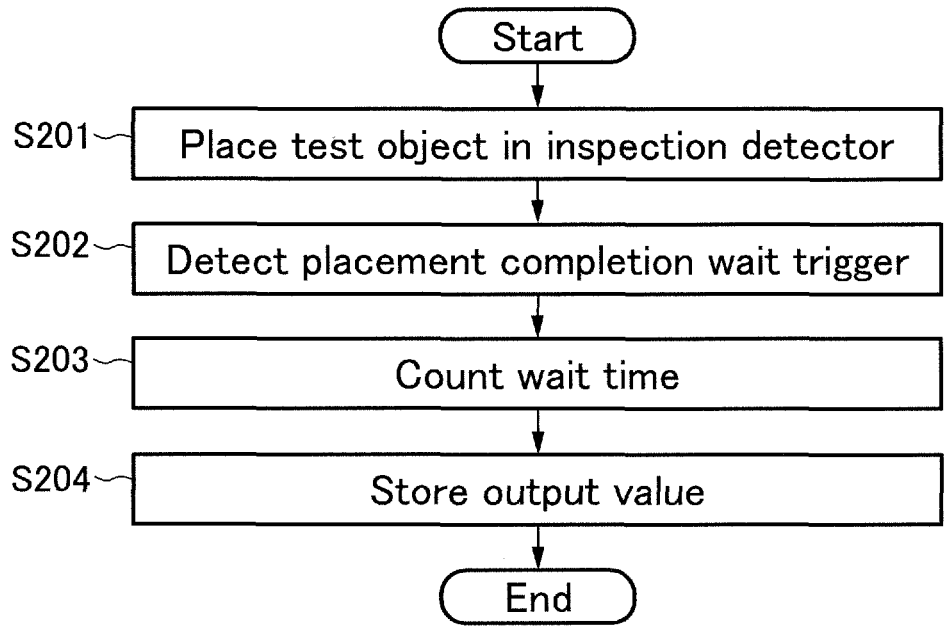
FIG. 7(A) is a flowchart showing the steps from placement of the test object up to start of measurement.

First, when a test object M is placed in the inspection detector 23 in step S201 shown in FIG. 7(A), the output value begins to decline starting at the initial offset value Ei0=3.000 when no test object M is placed, as shown in FIG. 6(A).

Next, in step S202, placement of the test object M in the inspection detector 23 is detected, and a trigger for the criterion to start the time count, which starts recording output values (start of the wait for measurement in FIG. 6(A)), is detected. In FIG. 6(A), reaching an output value of 1.500 is used as the placement completion wait trigger En1 to count waiting time in step S203. Note that the output value (1.500) which becomes the placement completion wait trigger En1 is set by a reverse calculation so that the output value stabilizes when a predetermined time explained in the following paragraph has elapsed.

Upon the elapse of a predetermined waiting time until the output value stabilizes (e.g., 2 to 3 seconds), measurement is performed in step S204 and a stabilized output value En2 (0.370) is detected and stored.

Since this enables a detection of the state of placement of the test object M in the inspection detector 23, i.e. of the fact that the test object M has been placed in a state whereby inspection can be correctly performed so that evaluation of test object surface properties can begin, measurement conditions can be made uniform and a stable output value En2 detected, and operator-caused variability, etc. can be eliminated and high accuracy measurement performed.

Control of removal of the test object M is performed as follows.

Figure 7B:
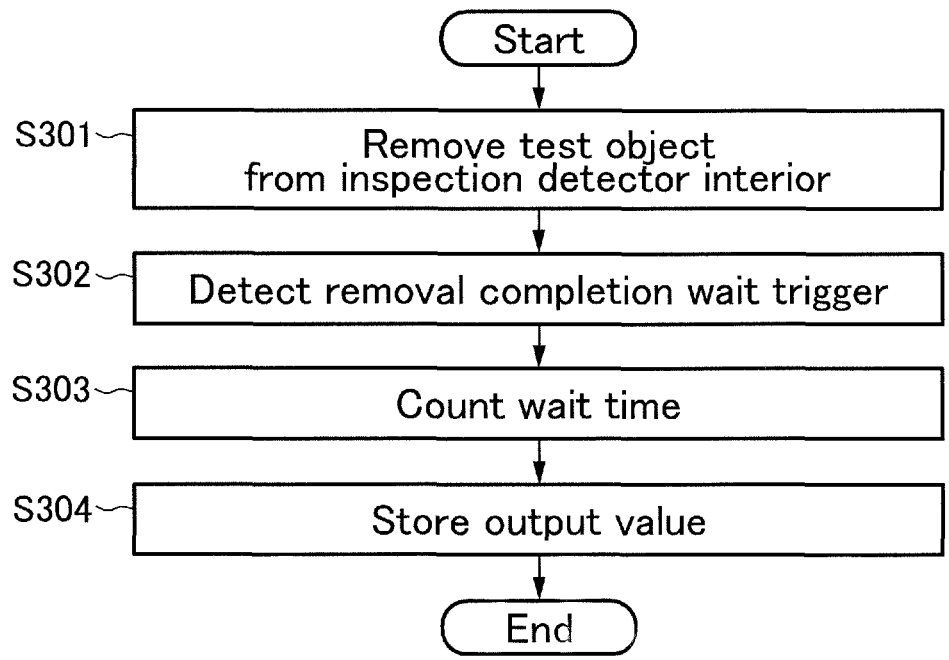
FIG. 7(B) is a flowchart showing the steps from measurement completion up to removal of the test object.

First, when a test object M is removed from an inspection detector 23 in the step S30 shown in FIG. 7(B), the measurement value starts to rise from the output value En2 observed when the test object M is placed, as shown in FIG. 6(B).

Next, in step S302, the removal completion wait trigger En3, which serves as the criterion for starting a count of the wait time to confirm removal of the test object (the start of waiting for completion in FIG. 6(B)), is detected. In FIG. 6(B), wait time is counted in step S303, using the time when the measurement value reaches 2.500 as the removal completion wait trigger En3. Note that the output value (2.500) for the removal completion wait trigger En3 is set by reverse calculation so that the output value becomes stable when the predetermined wait time described in the following paragraph elapses.

When a predetermined wait time (e.g., 2 to 3 seconds) elapses until the measurement value recovers to the vicinity of the initial value Ei0, the output value Ei1 (3.000) is detected in step S304 and stored.

At this point, the stored output value Ei1 can be used as the inspection offset value Eik.

Thus the fact that the test object M has been removed can be detected, and the next measurement performed with the measurement value returned to the initial state.

Using an arrangement in which control of placement and removal of a test object M is performed as described above, an apparatus can be simply constituted without the need to provide a position sensor or the like to detect whether a test object M has been appropriately placed relative to an inspection detector 23. Also, by adopting a system combining a transport means for transporting the test object M from a surface treatment apparatus for performing surface treatment to the surface property inspection apparatus 1 (e.g., a conveyor belt), or a sorting means for sorting inspected test objects M into good and bad parts, everything from surface treatment to inspection of the test object M can be performed consistently, and an automatable system can be built.

Variant Examples

When test state judgment step S7 is not implemented, surface property inspection apparatus 1 can omit the phase comparator 34. For example, a configuration can be used in which the positional relationship between the inspection detector 23 and the test object M is performed by a position detection means such as a laser displacement gauge, and a determination made using an optoelectric sensor (laser) or the like of whether the offset between the inspection detector 23 axis and the test object M axis are within a predetermined range. The phase comparator 34, frequency adjuster 35, or display means 37 can be integrated into a single piece by building them into the judgment means 36, for example.

If the output from the AC bridge circuit 20 when measuring the test object M is sufficiently large, variable resistor setting step S2 and frequency setting step S3 may be omitted. If the frequency setting step S3 is omitted, the surface property inspection apparatus 1 can omit the frequency adjuster 35.

Effect of the First Embodiment

Using the surface property inspection apparatus 1 and surface property inspection method of the present invention, an eddy current is excited in the test object M by the inspection detector 23 coil 23b, and the surface properties of the test object M can be evaluated by comparing the output signal output from the AC power supply 20 with the threshold value. This enables high precision inspection of the surface state using a simple circuit configuration.

Because a reference test object S of the same structure as the test object M is used to detect a reference state in the reference detector 22, fluctuations in output values due to changes in the inspection environment such as temperature, humidity, and magnetism will be the same as in the test object M. Fluctuations in output values caused by changes in the inspection environment such as temperature, humidity, or magnetism can thus be canceled and measurement accuracy improved. As in the claim 3 invention, use of an untreated part to which no surface treatment has been applied as the reference test object S enables the output, which is based on the difference in surface state relative to the test object M, to be increased, therefore measurement accuracy can be still further improved and the threshold value more easily set, which is preferable.

By only inspecting the surface properties of a test object subjected to a two stage shot peening comprising a first shot peening and a second shot peening after the second shot peening, an inspection of whether residual stress has been correctly imparted over a range of approximately 30-100 µm from the surface, for example, can be made to judge the quality of the first shot peening. By so doing, a judgment of whether the second stage peening has been correctly performed can be made by a single inspection after performing the two stage shot peening, thereby shortening inspection time. Inspection can also be quickly and non-destructively performed, making this method suitable for inline inspection, as well.

In addition to the above-described constitution, it is also possible to add imaging inspection after completion of the second shot peening.

By adding an image inspection, the reliability of the second shot peening pass/fail judgment can be further improved.

Second Embodiment

Two references are set for the frequency of the AC power supplied to the AC bridge circuit 20; inspection is performed with AC power supplied at different frequencies, and in addition to an inspection of whether residual stress was correctly applied after the first shot peening, an inspection can be made of whether residual stress was correctly applied after the second shot peening.

In the surface property inspection method of the present invention, information reflecting residual stress close to the surface is obtained in proportion to how high the AC power frequency supplied to the AC bridge circuit 20 is, and information reflecting the state of residual stress in a region deep below the surface is obtained in proportion to how low the AC power frequency is. Therefore setting a low frequency for the AC power supplied to the AC bridge circuit 20 enables inspection of whether residual stress has been correctly imparted after the first shot peening (first shot peening inspection step), and setting a high frequency enables inspection of whether residual stress has been correctly imparted after the second shot peening (second shot peening inspection step). Combining these inspections makes it possible to judge whether the first shot peening and second shot peening have respectively been correctly performed, thus enabling more accurate inspection. It is also possible to judge in a manner distinguishing which of the shot peenings was incorrect.

Here the frequency can be appropriately set according to the conductivity and magnetic permeability of the test object. When the test object is made of a steel material, setting the frequency to 20 to 50 kHz results in a detection depth, which is the eddy current penetration depth, of 60 to 100 µm from the outermost surface, therefore this is appropriate to inspection of whether the residual stress after the first shot peening has been correctly applied to the deep portion. Setting the frequency to 200 to 400 kHz results in a detection depth of 20 to 30 µm from the outermost surface, therefore this is appropriate to inspection of whether residual stress has been correctly imparted after the second shot peening. Hence in the above-described first embodiment, setting the frequency to 20 to 50 kHz enables a judgment of whether the first shot peening has been correctly performed.

(Pre-Measurement Settings)

When performing a first shot peening inspection step and a second shot peening inspection step, settings are made according to the respective inspection steps in frequency setting step S3 and threshold value setting step S4.

In the frequency setting step S3, setting of the frequency used in the first shot peening inspection is accomplished by preparing an untreated material and a test object treated by first shot peening; a frequency f1 is set, being the first frequency for which the difference in output voltage from the inspection apparatus is large in each test object. In the present embodiment, this setting value is 20 to 50 kHz.

In the frequency setting step S3, setting of the frequency used in the second shot peening inspection is accomplished by preparing an untreated material and a test object treated by only second shot peening, and a frequency f2 is set, being the second frequency with which the difference in output voltage from the inspection apparatus is large in each test object. In the present embodiment, this setting value is 200 to 400 kHz.

When inspecting with AC power at a frequency of 100 kHz or greater, as in the second shot peening inspection, there is a risk of generating surface effects due to the high frequency, which can cause conductor losses to increase and inspection sensitivity to diminish. If the coil 23b is formed using a Litz wire in which fine conducting strands of copper wire or the like are insulated by covering with enamel or the like and collected and twisted together as multiple fine conductor strands, the conductor surface area can be enlarged by refining the conductors, and conductor losses can be reduced, thereby enabling a favorable inspection sensitivity to be maintained.

In the threshold value setting step S4, setting of the initial threshold value Ethi1, which is the threshold value used for the first shot peening inspection, is performed by preparing an untreated part and a good part subjected to two stage shot peening, using the frequency f1 set in frequency setting step S3.

Setting of the initial threshold value Ethi2, which is the threshold value used for the second shot peening inspection, is performed by preparing an untreated part and a good part subjected to two stage shot peening, using the frequency f2 set in frequency setting step S3.

(Surface Property Inspection Method)

We will explain the surface property inspection method in the second embodiment by reference to FIGS. 8 and 9. Here we explain the case in which the second shot peening inspection is performed first, then the first shot peening inspection is performed (FIG. 9(A)). Note that changes in the output value in FIG. 9 are shown schematically for purposes of explanation.

In step S401, a test object M is placed in the inspection detector 23. The AC power supplied at this time is AC power at the frequency f2 used for the second shot peening inspection. Thus the step for exciting an eddy current in the test object M using AC power at frequency f2 corresponds to the second eddy current excitation step. When a test object M is placed in the inspection detector 23, the output value, as shown in FIG. 9(A), begins to drop from the initial value Ei0 when no test object M is in place.

Next, in step S402, placement of the test object M in the inspection detector 23 is detected, and placement completion trigger En1, which is the reference for starting a count of the time to start recording the output value (the start of waiting for measurement in FIG. 9(A)) is detected.

In the next step S403, waiting time is counted.

Upon the elapse of a predetermined waiting time until the output value stabilizes (e.g., 2 to 3 seconds), measurement is performed in step S404 and a stabilized output value En2 (1) is detected and stored.

In the next step S405, as a second pass/fail judgment step the output value En2 (2) is compared to the initial threshold value Ethi2; a second shot peening inspection is performed, and a judgment is made as to whether the second shot peening was correctly performed. If it is judged that the second shot peening was correctly performed (S405: YES), the system advances to step S406; if it is judged that the second shot peening was not correctly performed (S405: NO), the test object M is removed from the inspection detector 23 and measurement stopped, and the test object M is handled as a defective part.

In the following step S406, the frequency of the AC power supplied at this time is switched from the frequency f2 used in the second shot peening inspection to the frequency f1 used in the first shot peening inspection. By this means, an eddy current excitation step for exciting an eddy current in the test object M using AC power at frequency f1 is performed, and preparation for implementing a first shot peening inspection is made.

In the following step S407, waiting time is counted as the trigger point for switching frequencies. As shown in FIG. 9(A), the output value begins to rise, triggered by the switching of frequencies, starting with the output value En2(2).

Upon the elapse of a predetermined waiting time until the output value stabilizes (e.g., 5 to 6 seconds), measurement is performed in step S408 and a stabilized output value En2 (1) is detected and stored.

In the next step S409, as a second pass/fail judgment step the output value En2 (1) is compared to the initial threshold value Ethi1; a first shot peening inspection is performed, and a judgment is made as to whether the first shot peening was correctly performed. If it is judged that the first shot peening was correctly performed (S409: YES), the system advances to step S410; if it is judged that the second shot peening was not correctly performed (S409: NO), the test object M is removed from the inspection detector 23 and measurement stopped, and the test object M is handled as a defective part.

In the following step S410, the test object M, for which it is judged that the first shot peening and second shot peening have been correctly performed, is removed from the inspection detector 23. When the test object M is removed from the inspection detector 23, the output value begins to rise from the output value En2(1) observed when the test object M was placed therein.

In the following step S411, the removal completion wait trigger En3, which serves as the criterion for starting a count of the wait time to confirm removal of the test object M (the start of waiting for completion in FIG. 9(A)), is detected.

In the next step S412, waiting time is counted.

When a predetermined wait time (e.g., 1 to 2 seconds) until the measurement value recovers to the vicinity of the initial value Ei0 has elapsed, the output value Ei1 (3.000) is detected in step S413 and stored. Thus the fact that the test object M has been removed can be detected, and the next measurement performed with the measurement value returned to the initial state.

Using the above-described surface property inspection method, inspection can be performed by a first shot peening inspection step of whether the correct residual stress has been imparted after the first shot peening, and inspection can be performed by a second shot peening inspection step of whether the correct residual stress has been imparted after the second shot peening. This makes it possible to judge whether the first shot peening and second shot peening have respectively been correctly performed, thus enabling more accurate inspection. It is also possible to judge in a manner distinguishing which of the shot peenings was incorrect. The initial threshold value Ethi1 used in the first shot peening inspection step and initial threshold value Ethi2 used in the second shot peening inspection step are respectively set according to the frequency used in the inspection, therefore an accurate judgment can be made of whether the first shot peening and second shot peening have been correctly performed.

Variant Examples

In the above-described embodiment, the first shot peening inspection step was performed after the second shot peening inspection step, but the second shot peening inspection step can also be performed after the first shot peening inspection step. In such cases, the first shot peening inspection step is performed in steps S402-S405, and the second shot peening inspection step is performed in steps S407-S409. Changes in the output value in this case would be as shown in FIG. 9(B). Note that because the response speed of the output value at the time of inspection is faster with a higher frequency, inspection time can be shortened by first performing the second shot peening inspection step, in which the supplied AC power has a higher frequency.

Effect of the Second Embodiment

Using the surface property inspection method of the second embodiment, inspection can be performed by a first shot peening inspection step of whether the correct residual stress has been imparted after the first shot peening, and inspection can be performed by a second shot peening inspection step of whether the correct residual stress has been imparted after the second shot peening. This makes it possible to judge whether the first shot peening and second shot peening have respectively been correctly performed, thus enabling more accurate inspection. It is also possible to judge in a manner distinguishing which of the shot peenings was incorrect.

EXPLANATION OF REFERENCE NUMERALS

1: surface property inspection apparatus
10: AC power supply
20: AC bridge circuit
21: variable resistor
22: reference detector
23: inspection detector
23a: core
23b: coil
23c: magnetic shield
30: evaluation device
31: amplifier
32: absolute value circuit
33: LPF
34: phase comparator
35: frequency adjuster
36: judgment means
37: display means
38: temperature measurement means
M: test object
S: reference test object

The invention claimed is:

1. A surface property inspection method for inspecting a surface property of a shot peened test object, comprising steps of:
   an inspection apparatus preparation step for preparing a surface property inspection apparatus, wherein the surface property inspection apparatus comprises:
      an AC bridge circuit;
      an AC power supply for supplying AC power to the AC bridge circuit; and
      an evaluation device for evaluating the surface property of the test object based on an output signal from the AC bridge circuit;
   wherein the AC bridge circuit comprises:
      a variable resistor configured to vary a divide ratio between a first resistor and a second resistor,
      an inspection detector comprising a coil capable of exciting AC magnetism, said coil being configured to excite an eddy current in the test object disposed adjacent to the coil, and
      a reference detector, in which a reference test object having the same structure as the test object is disposed, and detecting a reference state which serves as a reference for comparison with an output from the inspection detector; and
   wherein the first resistor, the second resistor, the reference detector, and the inspection detector constitute the bridge circuit;
   a threshold value setting step for determining a threshold value used in evaluating the surface property of the test object in the evaluation device;
   an eddy current excitation step for exciting the eddy current by the inspection detector in the test object, simultaneously with exciting the eddy current by the reference detector in the reference test object, wherein the test object is subjected to a first shot peening for imparting residual stress from a surface into deep portions and then subjected to a second shot peening for performing a lower strength shot peening than the first shot peening, thereby imparting further residual stress from the surface into shallow portions in comparison with the first shot peening; and
   a pass/fail judgment step for using the evaluation device to compare the threshold value with the output signal output from the AC bridge circuit during the eddy current excitation step implemented after the second shot peening, and then judging whether the first shot peening was correctly performed
   wherein in the eddy current excitation step, a frequency of the AC power supplied to the AC bridge circuit is set so that the eddy current reaches to a depth to which the residual stress is imparted by the first shot peening.

2. The method of claim 1, wherein the eddy current excitation step is performed under the state that the reference test object which is an untreated object, not subjected to surface treatment, is placed in the reference detector.

3. The method of claim 1, wherein in the threshold value setting step, the threshold value is determined based on the output signal from the AC bridge circuit when the eddy current is excited in the test object on which the first shot peening and second shot peeing have been correctly performed.

4. The method of claim 1, further comprising steps of:
   a second eddy current excitation step wherein which AC power at a higher frequency than that of the eddy current excitation step is supplied by the AC power supply to excite the eddy current in the test object, and
   a second pass/fail judging step wherein the evaluation device judges whether the second shot peeing has been appropriately performed, based on the output signal from the AC bridge circuit when the eddy current is excited during the second eddy current excitation step.

5. The method of claim 4, wherein the threshold value setting step determines the threshold value determined based on the output signal obtained by supplying a predetermined first frequency AC power to the AC bridge circuit, and a second threshold value determined based on the output signal obtained by supplying a predetermined second frequency AC power to the AC bridge circuit, the second frequency is higher than the first frequency and the threshold value is used to make a pass/fail judgment in the pass/fail judgment step and the second threshold value is used to make the pass/fail judgment in the second pass/fail judgment step.

6. The method of claim 4, wherein the second pass/fail judgment step is performed before the pass/fail judgment step.

7. The method of claim 3, wherein in the threshold value setting step, by using an output signal EA from the AC bridge circuit when an untreated test object is disposed in the inspection detector, and an output signal EB from the AC bridge circuit when the test object on which the first shot peening and the second shot peening have been correctly performed is disposed in the inspection detector, the threshold value Ethi is determined according to the expression:

$Ethi = (EAav \cdot \sigma B + EBav \cdot \sigma A)/(\sigma A + \sigma B)$, where EAav: average value of the output signal EA; EBav: average value of the output signal EB; σA: standard deviation in the output signal EA; σB: standard deviation in the output signal EB.

8. The method of claim 1, wherein the evaluation device comprises a memory device by which identifying information for each test object, and surface property inspection data for said test object, are correlated and stored.

9. A surface property inspection apparatus for inspecting a surface property of a test object subjected to a first shot peening for imparting residual stress from a surface into deep portions by a shot peening apparatus, and a second shot peening for performing, after the first shot peening, a lower strength shot peening than the first shot peening, thereby imparting further residual stress from the surface into shallow portions in comparison with the first shot peening, the apparatus comprising:
   an AC bridge circuit;
   an AC power supply for supplying AC power to the AC bridge circuit; and
   an evaluation device for evaluating the surface property of the test object based on an output signal from the AC bridge circuit;
   wherein the AC bridge circuit comprises:
      a variable resistor configured to vary a divide ratio between a first resistor and a second resistor,
      an inspection detector comprising a coil capable of exciting AC magnetism, said coil being configured to excite an eddy current in the test object disposed adjacent to the coil, and
      a reference detector in which a reference test object having the same structure as the test object is disposed, and detecting a reference state which serves as a reference for comparison with an output from the inspection detector;
   wherein the first resistor, the second resistor, and the reference detector and the inspection detector constitute the bridge circuit, and
   wherein after the second shot peening, the evaluation device evaluates the surface property of the test object to judge whether the first shot peening has been properly performed on the test object by comparing a threshold value and the output signal from the AC bridge circuit, wherein the output signal is obtained by applying AC power to the AC bridge circuit in a state that the inspection detector detects electromagnetic property of the test object, while the reference detector detects the reference state,
   wherein the AC power supply supplies the AC bridge circuit with the AC power at a frequency selected so that the eddy current reaches to a depth to which the residual stress is imparted by the first shot peening.

10. The apparatus of claim 9, wherein the reference test object is an untreated object not subjected to surface treatment.

11. The apparatus of claim 9, wherein the coil is formed of Litz wire.

* * * * *